US00RE42832E

(19) United States
(12) Reissued Patent
Nagel et al.

(10) Patent Number: US RE42,832 E
(45) Date of Reissued Patent: Oct. 11, 2011

(54) METHOD FOR REFORMING ORGANICS INTO SHORTER-CHAIN UNSATURATED ORGANIC COMPOUNDS

(75) Inventors: Christopher J. Nagel, Wayland, MA (US); Thomas P. Griffin, Kennett Township, PA (US); Thomas A. Kinney, Boston, MA (US); Kevin A. Sparks, Scituate, MA (US)

(73) Assignee: Quantum Catalytics, L.L.C., Fall River, MA (US)

(21) Appl. No.: 10/616,797

(22) Filed: Jul. 10, 2003
(Under 37 CFR 1.47)

Related U.S. Patent Documents

Reissue of:
(64) Patent No.: 6,258,988
Issued: Jul. 10, 2001
Appl. No.: 08/172,579
PCT Filed: Dec. 23, 1993

(51) Int. Cl.
*C10G 9/34* (2006.01)
*C07C 2/88* (2006.01)
*C07C 4/02* (2006.01)

(52) U.S. Cl. ..... 585/241; 585/541; 585/634; 585/637; 585/638; 585/648; 585/650; 585/653; 585/912; 585/942; 585/943; 208/126; 208/404; 208/504; 208/406; 588/201

(58) Field of Classification Search ..... 585/241, 585/541, 634, 637, 638, 648, 650, 653, 912, 585/942, 943; 588/201; 266/242, 217, 265, 266/268
See application file for complete search history.

(56) References Cited

U.S. PATENT DOCUMENTS

| | | | | |
|---|---|---|---|---|
| 2,858,255 A | | 10/1958 | Segui et al. | 202/219 |
| 3,974,206 A | * | 8/1976 | Totsumi et al. | 585/241 X |
| 3,996,022 A | * | 12/1976 | Larsen | 44/1 D |
| 4,012,457 A | | 3/1977 | Bredeson et al. | 260/683 |
| 4,149,853 A | * | 4/1979 | Demarais, Jr. et al. | 44/50 |
| 4,552,667 A | * | 11/1985 | Shultz | 210/757 |
| 4,574,038 A | | 3/1986 | Wan | 204/162 |

(Continued)

FOREIGN PATENT DOCUMENTS

| | | |
|---|---|---|
| DE | 1618182 | 12/1970 |
| DE | 2058553 | 2/1974 |
| EP | 0 067 491 A2 | 12/1982 |
| GB | 936899 | 9/1963 |
| GB | 44-11648 | 5/1969 |
| GB | 1270074 | 4/1972 |
| GB | 1350612 | 4/1974 |
| GB | 2088893 | 6/1982 |
| GB | 399526 | 9/1993 |
| WO | 93/02751 | 2/1993 |

OTHER PUBLICATIONS

Adams et al., "Dehydrogenation and Coupling Reactions in the Presence of Iodine and Molten Salt Hydrogen Iodide Acceptors," *Journal of Organic Chemistry*, 42(1) :1-6 (1977).

(Continued)

*Primary Examiner* — Thuan Dinh Dang
(74) *Attorney, Agent, or Firm* — Carolyn S. Elmore, Esq.; Darlene A. Vanstone, Esq.; Elmore Patent Law Group

(57) ABSTRACT

A method is disclosed for reforming organics into shorter-chain unsaturated organic compounds. A molten metal bath is provided which can cause homolytic cleavage of an organic component of an organic-containing feed. The feed is directed into the molten metal bath at a rate which causes partial homolytic cleavage of an organic component of the feed. Conditions are established and maintained in the reactor to cause partial homolytic cleavage of the organic component to produce unsaturated organic compounds, as products of the homolytic cleavage, which are discharged from the molten metal bath.

19 Claims, 1 Drawing Sheet

U.S. PATENT DOCUMENTS

| | | | | |
|---|---|---|---|---|
| 4,574,714 | A | 3/1986 | Bach et al. | 110/346 |
| 4,666,696 | A | 5/1987 | Shultz | 423/659 |
| 4,769,507 | A * | 9/1988 | Murib et al. | 585/500 |
| 5,177,304 | A | 1/1993 | Nagel | 588/201 |
| 5,191,154 | A * | 3/1993 | Nagel | 588/201 |

OTHER PUBLICATIONS

Saito et al., "Dehydrogenation of Some Alcohols by the Molten Metal Catalysts," *Bulletin of the Japan Petroleum Institute*, 14(2) :169-173 (1972).

Kashiwadate et al., "The Dehydrogenation of Butyl Alcohols by the Molten-metal Catalysts," *Bulletin of the Chemical Society of Japan*, 44(11) :3004-3009 (1971).

Haggin, J., "Growth and Dissociation of Metal-Carbon Nanocrystals Probed," *Chem. & Eng. News*, pp. 29-32, Oct. 25, 1993.

Haggin, J., "European Conference Draws Attention to Fundamental Role of Catalysis," *Chem & Eng. News*, pp. 26-30, Oct. 18, 1993.

Layman, P.L., "Advances in Feedstock Recycling Offer Help with Plastic Waste," *Chem & Eng. News*, pp. 11-14, Oct. 4, 1993.

Satterfield, C.N., "Acid and Zeolite Catalysts," In Gail F. Nalven (Ed.), *Heterogeneous Catalysis in Industrial Practice*, 2nd Ed., (NY: McGraw-Hill), pp. 209-266, pp. 339-417, (1991).

Jebens, A.M., "CEH Marketing Research Report, Ethylene," *Chemical Economics Handbook—SRI International*, (Report Olefins 432. 000 A) Sep. 1992.

* cited by examiner

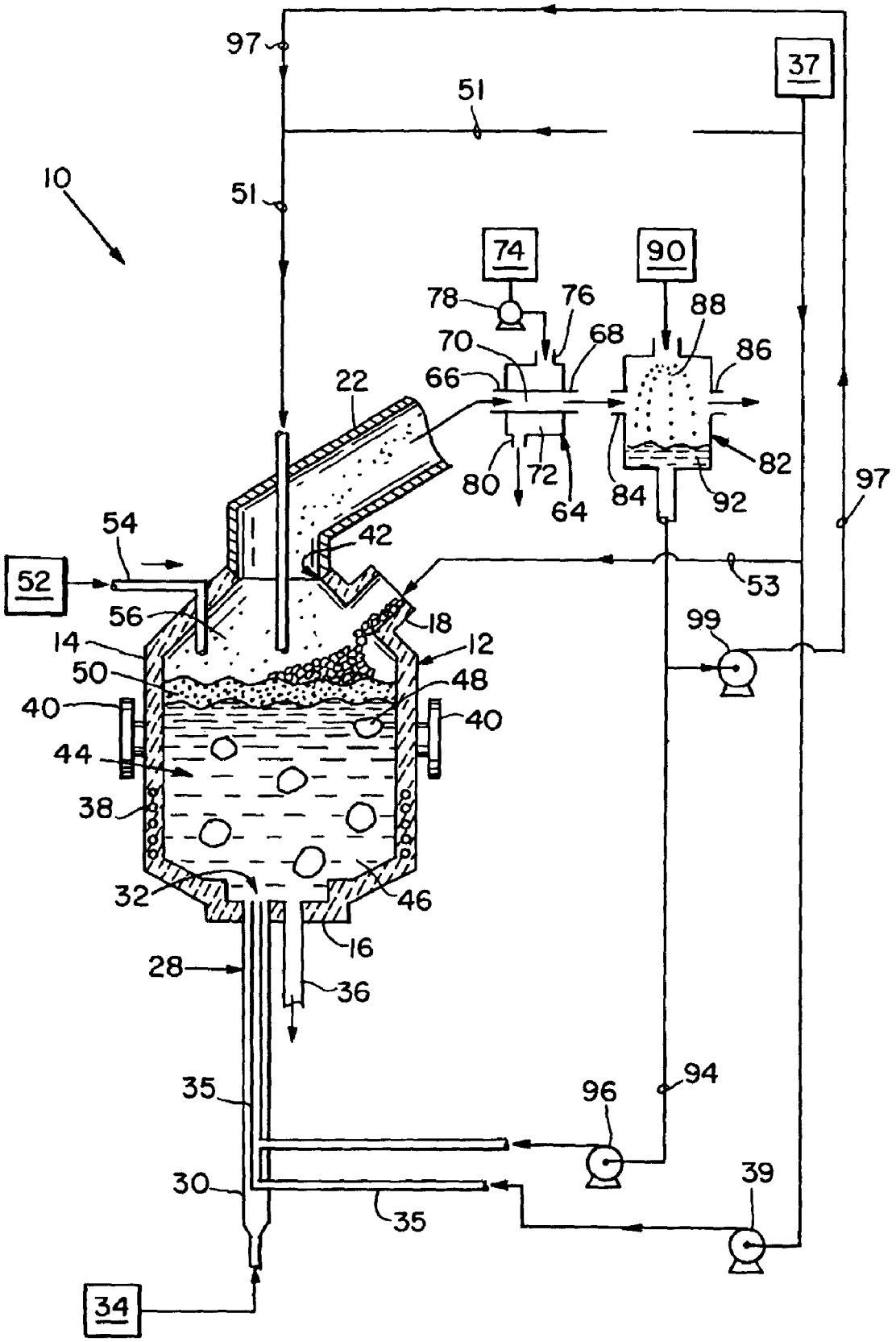
97
51
37
10
51
74
90
78
76
88
70
68
86
66
22
82
80
72
64
84
92
97
54
42
52
53
56
18
99
14
12
50
48
40
40
44
38
32
46
16
28
36
35
96
94
30
39
35
34

METHOD FOR REFORMING ORGANICS INTO SHORTER-CHAIN UNSATURATED ORGANIC COMPOUNDS

Matter enclosed in heavy brackets [ ] appears in the original patent but forms no part of this reissue specification; matter printed in italics indicates the additions made by reissue.

BACKGROUND OF THE INVENTION

Considerable research has been conducted recently in the area of producing olefins for use as industrial raw materials. Among the many uses of such commodity chemicals include plastic and fibers for consumption in packaging, transportation and construction industries. Of particular interest are areas of research focusing on production of olefins, such as ethylene, which is consumed principally in the manufacture of polyethylene, and substituted alkenes, such as ethylene dichloride and vinyl chloride. Ethylene is also employed in the production of ethylene oxide, ethyl benzene, ethylene dichloride, ethylene-propylene elastomers and vinyl acetate.

The primary sources of olefins, such as ethylene include: steam cracking of organics, such as gas oils; off-gas from fluid catalytic cracking (FCC) in oil refineries, catalytic dehydration of alcohols; and recovery from coal-derived synthesis gas. However, the worldwide demand for olefins is extraordinary: the short fall in worldwide supply of ethylene alone was estimated in 1991 to be about 2.3 million tons, as determined by the Chemical Economics Handbook, SRI International (1992). Further, known methods for producing olefins have significant drawbacks. For example, organic steam-cracking, which accounts for about 100% of ethylene production in the United States, is a mature technology which is highly sensitive to process variables, such as cracking severity, residence time and hydrocarbon partial pressure, as well as plant economics and price fluctuation. In addition, such processes are facing increasing environmental regulatory pressure to control systemic problems, such as leaks and failure from related equipment and safety concerns associated with olefin cracking.

Other listed production methods have even greater limitations. The availability of FCC off-gas, for example, generally prohibits its use as an economically viable feed stock. Catalytic dehydration of alcohols is effectively limited to certain countries that have large amounts of readily available fermentation raw material. Also, known methods for production of olefins from other sources, such as coal and coal-derived naphtha and methanol are, at best, only marginally commercially viable.

Therefore, a need exists for an improved method of producing olefins which significantly reduces or eliminates the above-mentioned problems.

SUMMARY OF THE INVENTION

The invention relates to a method for reforming organics into shorter-chain unsaturated organic compounds.

A molten metal bath is provided which can cause homolytic cleavage of an organic component of an organic-containing feed. The feed is directed into the molten metal bath at a rate which causes partial homolytic cleavage of the organic component of the feed. Conditions are established and maintained in the reactor to cause partial homolytic cleavage of the organic component to produce shorter-chain unsaturated organic compounds, which are discharged from the molten metal bath.

The present invention has many advantages. For example, the present invention provides good control over production of organics, such as alkenes, including ethylene. Also, high yields of ethylene are obtained by the present invention. The present method is a recycling process, employing solution equilibria to synthesize commercial products, such as methane, ethane and propane, from a wide variety of organic feeds, including most hazardous industrial wastes. The present invention also has the ability to sustain high product quality, irrespective of feed heterogeneity, including chemical or physical complexity. In addition, the invention provides flexibility to engineer the properties and composition of a ceramic phase generated by the method. Further, the present invention has the ability to recover and recycle volatile and nonvolatile materials.

BRIEF DESCRIPTION OF THE DRAWING

The FIGURE is a schematic representation of one embodiment of apparatus suitable for conducting the method of the invention.

DETAILED DESCRIPTION OF THE INVENTION

The features and other details of the method of the invention will now be more particularly described with reference to the accompanying figures and pointed out in the claims. It will be understood that particular embodiments of the invention are shown by way of illustration and not as limitations of the invention. The principal functions of this invention can be employed in various embodiments without departing from the scope of the invention.

The present invention generally relates to a method reforming organic components of a feed into shorter-chain unsaturated organic compounds. An example of a suitable feed includes an organic waste. Processes for decomposing waste in molten metal baths are disclosed in U.S. Pat. Nos. 4,574,714, 5,177,304, and 4,602,574 which are incorporated herein by reference.

In one embodiment of the invention, illustrated in FIG. 1, system 10 includes reactor 12. Examples of suitable vessels include those described in U.S. Ser. No. 08/041,490 and U.S. Ser. No. 08/041,405, the teachings of which are incorporated herein by reference, and reactors which are described in U.S. Pat. Nos. 4,574,714, 5,177,304, and 4,602,574. Reactor 12 has an upper portion 14 and a lower portion 16. Feed inlet 18 at upper portion 14 of reactor 12 is suitable for directing feed into reactor 12. Off-gas outlet 22 extends from upper portion 14 and is suitable for conducting an off-gas out of reactor 12.

It is to be understood that the feed stream is generally introduced to molten metal bath 44 without injection of a coolant if reaction of the feed in reaction 12 is endothermic. However, tuyere 28 is dimensioned and configured for conjointly and continuously introducing a suitable feed stream and coolant into reactor 12. Tuyere 28 includes coolant tube 30 and feed inlet tube 35. Coolant tube 30 extends from coolant source 34 to reactor 12. Feed inlet tube 35 extends from feed source 37 to tuyere 28. Feed inlet tube 35 is disposed at tuyere opening 32. Pump 39 is disposed at tuyere 28 to direct a suitable feed stream from feed source 37 and through tuyere opening 32 into reactor 12.

It is to be understood that an oxidant can also be fed to reactor 12 through tuyere 28 and/or at other locations within reactor 12, as are taught in U.S. Pat. No. 5,191,154, the teachings of which are incorporated by reference. It is also to be understood that more than one tuyere 28 can be disposed in reactor 12 and that concentric, or multiple concentric tuyeres, can be employed for separate introduction of the feed stream into reactor 12. Further, it is to be understood that feed can be introduced into reactor 12 by other suitable methods, such as by employing a lance, etc.

Bottom-tapping spout 36 extends from lower portion 16 and is suitable for removal of at least a portion of a molten bath from reactor 12. Additional drains can be provided as a means of continuously or intermittently removing distinct molten phases. Material can also be removed by other methods, such as are known in the art. For example, material can be removed from reactor 12 by rotating vessel 12 and employing a launder, not shown, extending from feed inlet 18. Alternatively, the launder can extend into reactor 12 through a tap hole, also not shown.

Induction coil 38 is disposed at lower portion 16 for heating reactor 12 or for initiating generation of heat within reactor 12. It is to be understood that, alternatively, reactor 12 can be heated by other suitable means, such as by plasma torch, electric arc, etc. Trunions 40 are disposed at reactor 12 for manipulation of reactor 12. Seal 42 is disposed between reactor 12 and off-gas outlet 22 and is suitable for allowing partial rotation of reactor 12 about trunions 40 without breaking seal 42. Alternatively, reactor 12 does not include trunions 40 or seal 42 and does not rotate.

Molten metal bath 44 is disposed within reactor 12. In one embodiment, molten metal bath 44 includes a metal which, when molten, causes at least a portion of saturated hydrocarbon in the injected feed to be reformed to at least one unsaturated alkene, such as ethylene, under the operating conditions of system 10. In one embodiment, the metals of molten metal bath 44 have a melting point in the range of between about 900° C. and 1,100° C. The melting point of bath 44 is low enough to cause the organic components of the injected feed to be reformed by homolytic cleavage and to be subsequently discharged from bath 44 as at least one unsaturated organic compound.

In a particularly preferred embodiment, the operating conditions of the bath include, for example, temperatures which prevent substantial degradation of organic compounds. Also, the required residence times of the feed in the bath of molten metal are substantially shorter than are those typically employed to thermally decompose organic-containing feeds.

Preferably, the carbon concentration in bath 44 is at a relatively low level, such as a concentration which is substantially below the saturation limit for the bath at the operating conditions of reactor 12. The amount of carbon in molten metal bath 44 can be controlled, for example: by the rate of introduction of the feed stream, to molten metal bath 44; by controlling the rate of removal of off-gas from molten metal bath 44; by controlling system conditions, e.g., temperature, of system 10; by controlling the relative amounts of other components in molten metal bath 44; etc. For example, the organic-containing feed can be directed into molten metal bath 44 at a rate which causes the residence time of a carbon component of the feed to be greater than that required to cause molten metal bath 44 to dissolve the carbon under the operating conditions established and maintained in the reaction zone.

The thermal history of the organic compounds in the reaction zone is affected by the reaction zone temperature, residence time of the compounds in the reaction zone, and various intensive properties associated with materials in the reaction zone. The effective operating temperature is that temperature to which organic species of interest are exposed while they are in the reaction zone. This temperature is chosen so as to maximize the conditions which lead to product formation while minimizing any subsequent product degradation reactions. The effective temperature can be achieved under conditions supporting thermal equilibrium (e.g., having low temperatures in the reaction zone and relatively long residence times) or under conditions that prevent thermal equilibrium (e.g., very high temperatures in the reaction zone with relatively short residence times). For example, if the optimal product formation occurs at a substrate temperature of 900° C., this could be achieved with a liquid metal operating at 900° C. and allowing sufficient residence time for the product to reach thermal equilibrium or it could be achieved by injecting it into a high temperature reaction zone (e.g., 2000° C.) for a very short period of time thereby providing insufficient time for the product to reach thermal equilibrium (i.e., allowing the product to exit the reaction zone at 900° C.). "Homolytic cleavage," as defined herein, means cleavage of at least one carbon-carbon bond of the organic component of the feed directed into reactor 12 to form, for example, an organic compound having fewer carbon atoms. "Partial homolytic cleavage," as defined herein means that the homolytic cleavage product includes at least one organic compound.

Examples of suitable metals in molten metal bath 44 include transition metals and, in particular, transition metals which have carbon solubility. Examples of especially suitable transition metals include iron, chrome, vanadium, copper, aluminum, etc. It is to be understood that molten metal bath 44 can include oxides of the molten metals. As disclosed in U.S. Pat. No. 5,177,304, the teachings of which are incorporated herein, molten metal bath 44 can include more than one phase of molten metal. In one embodiment, molten metal bath 44 is formed of a ceramic phase which includes at least one metal oxide. In another embodiment, the ceramic phase can include at least one salt. Alternatively, a substantial portion of molten metal bath 44 can be of elemental metal.

Molten metal bath 44 can be formed by at least partially filling reactor 12 with a suitable metal. The metal is then heated to a suitable temperature by activating induction coil 38 or by other means, not shown. Optionally, two immiscible metals can be introduced to reactor 12, whereby the metals separate during melting to form two distinct molten metal phases. In one embodiment, the viscosity of at least one phase of molten metal bath 44 is less than about ten centipoise at the operating conditions of system 10. In another embodiment, the viscosity of at least one phase of molten metal bath 44 is less than about thirty poise at the operating conditions of system 10.

Suitable operating conditions of system 10 include a temperature sufficient to chemically react feed from feed source 37 and thereby form at least one metallic carbide. "Metallic carbide," as that term is used herein, means a compound or complex which is a product of a reaction or some other interaction between a metal and a component of a feed stream directed into molten metal bath 44.

Ceramic layer 50 is disposed on molten metal bath 44. Ceramic layer 50 is substantially immiscible with molten metal bath 44. Alternatively, system 10 does not include ceramic layer 50. The solubility of carbon in ceramic layer 50 can be less than that of molten metal bath 44, thereby causing atomic carbon to be retained within molten metal bath 44. In another embodiment, ceramic layer 50 has a lower thermal conductivity than that of molten metal bath 44. Radiant loss of heat from molten metal bath 44 can thereby be reduced to significantly below the radiant heat loss from molten metal bath 44 when no ceramic layer 50 is present.

Examples of suitable metal oxides of ceramic layer 50 include titanium oxide ($TiO_2$), zirconium oxide ($ZrO_2$), aluminum oxide ($Al_2O_3$), magnesium oxide (MgO), calcium oxide (CaO), silica ($SiO_2$), etc. Other examples of suitable components of ceramic layer 50 include halogens, sulfur, phosphorus, heavy metals, etc. It is to be understood that ceramic layer 50 can include more than one metal oxide. Ceramic layer 50 can contain more than one phase. Typically, ceramic layer 50 is substantially fluid and free radicals and other gases can pass across ceramic layer 50 from molten metal bath 44.

Ceramic layer 50 can be formed by directing suitable materials, such as metals, metal oxides, halogens, sulfur, phosphorus, heavy metals, sludges, etc., from source 52 through inlet tube 54 and into molten metal bath 44. The materials from source 52 can be directed onto the top of molten metal bath 44 or injected into molten metal bath 44, using methods such as are well-known in the art. The materials can form other stable compounds at the operating conditions of system 10 by reaction, for example, with alkali metal cations or alkaline earth metal cations. Examples of such stable reaction products include calcium fluoride ($CaF_2$) and magnesium phosphate ($Mg(PO_4)_2$). In one embodiment, ceramic layer 50 contains about forty percent calcium oxide, about forty percent silicon dioxide, and about twenty percent aluminum oxide, and is about five inches thick.

Feed, such as an organic-containing waste in solid, liquid, or gaseous form, is directed from feed source 37 into a reaction zone within reactor 12. The reaction zone is defined to be the region in which the product formation reaction(s) occur. It can include the volume within the reactor and within attached off-gas handling equipment. The conditions supporting reaction includes liquid metal system, the gas/liquid interface, and the gas above the liquid metal which contains metal vapor and reactive metal particles and droplets (such as can be formed by entrainment).

The feed can be introduced to reactor through line 35, line 51 and/or line 53. The feed includes at least one organic component. Examples of suitable organic components include methane, ethane, and propane. Examples of suitable alkyl hydrocarbons include n-hexane and polyethylene. Examples of suitable feeds include "dirty" crude oil, bottoms from oil refineries, oil shales, hazardous wastes, etc.

In one embodiment, the feed is injected into molten metal bath 44 as a component of a feed stream that also includes an inert gas component, such as argon. In one example, the feed stream is formed by vaporizing liquid organic feed in the presence of an inert gas. The amount of volatilized feed component in the feed stream can be, for example, in the range of between about five and forty percent. In addition to hydrogen and carbon, the organic component of the feed stream can also include other atomic constituents, such as halides, metals, etc.

The feed stream directed into reactor 12 combines with molten metal bath 44 and can also combine with ceramic layer 50. The feed stream and coolant are directed into molten metal bath 44 through tuyere 28. The feed stream can also be directed into reactor 16 from feed source 37 through conduit 51. Conduit 51 discharges the feed beneath the surface of molten metal bath 44. Contact of the feed with molten metal bath 44 or ceramic layer 50 exposes the feed to conditions sufficient to form an unsaturated organic product.

Consistent with the reaction zone definition, the reaction can be carried out predominantly in the liquid metal phase, the space immediately above the condensed liquid metal phase, or in the gas space above the condensed reaction media bath provided that sufficient concentrations of vapor, droplets, particles, etc., exist to support the necessary reaction rates. Optionally, at least a portion of molten metal bath 44 can be suspended by gas directed through tuyere 28. Suspended molten metal bath 44 can be a continuum of metal extending through a generally gaseous volume or a region of particulate molten metal suspended in a generally gaseous volume within reactor 12.

At least one metal component of the bath of molten metal causes the saturated hydrocarbon feed to dissociate to form unsaturated alkenes through a metallic carbide. The metal carbide is formed under the operating conditions of the bath of molten metal which are established and maintained according to the method of the invention. The operating conditions can include, for example, low effective bath temperature, carbon solubility of the bath, and short contact and residence times of the organic component in the bath. Examples of particular embodiments of suitable operating conditions include: a bath temperature in the range of between 900° C. and 1,100° C.; solubilities for carbon exhibited by aluminum, copper and brass at that temperature; and residence times of the organic component sufficient to achieve thermal equilibrium in the bath of molten metal in the range of between 0.1 and 5 seconds, or less than 0.1 seconds if thermal equilibrium is not achieved. "Thermal equilibrium," as defined herein, means that the temperature within the reaction zone is substantially uniform.

If necessary, a coolant can be employed to cool tuyere 28. Examples of suitable coolants include steam, methane ($CH_4$), hydrogen gas ($H_2$), etc.

Gaseous layer 56 is formed over ceramic layer 50. In one embodiment, gaseous layer 56 extends from upper portion 14 of reactor 12 through off-gas outlet 22 to scrubber 82. A reaction zone within system 10 includes molten metal bath 44, ceramic layer 50 and gaseous layer 56. Reactants, can be introduced anywhere within the reaction zone. Gaseous layer 56 includes off-gas formed in molten metal bath 44 and in ceramic layer 50. The off-gas includes reaction products, such as unsaturated organic compounds formed in molten metal bath 44. The off-gas can also include at least one intermediate component which has been entrained or which has been volatilized before reformation to a shorter-chain unsaturated alkene is complete.

off-gas formed in reactor 12 is conducted from the reaction zone through off-gas outlet 22 to heat exchanger 64. Heat exchanger 64 can be any suitable heat exchanger for cooling off-gas discharged from reactor 12. Examples of suitable heat exchangers include water-cooled hoods, shell-and-tube heat exchangers, fluid beds, etc. Examples of off-gas components include unreacted or fragmented portions of the organic-containing component.

The off-gas is conducted into heat exchanger 64 through heat exchanger off-gas inlet 66 and then through heat-exchanger off-gas outlet 68. Optionally, the off-gas is cooled in heat exchanger 64 by conducting the off-gas through an off-gas side 70 of heat exchanger 64 and by directing a suitable cooling medium through a medium-side 72 of heat exchanger 64. Examples of suitable cooling mediums include, for example, water, ethylene glycol, ethyl benzene, alcohols, etc. The cooling medium is directed from cooling medium source 74 through cooling medium inlet 76 of heat exchanger 64 by a suitable means, such as by use of pump 78 disposed between cooling medium source 74 and heat exchanger 64. The cooling medium is directed through the medium side 72 of heat exchanger 64, thereby cooling the off-gas, and then directed out of heat exchanger 64 through cooling medium outlet 80.

The off-gas is directed out of heat exchanger off-gas outlet 68 to a suitable separating means for exposing the off-gas to conditions sufficient to remove at least a portion of an intermediate component from the off-gas. In one illustration, the separating means is scrubber 82. The off-gas is directed through scrubber off-gas inlet 84 and then through scrubber 82 to scrubber off-gas outlet 86.

Scrubber fluid 88 is directed from scrubber fluid source 90 to scrubber 82 by a suitable means, such as by gravity or by a pump, not shown. Scrubber fluid 88 is introduced to scrubber 82 at a temperature suitable for removing at least a portion of the component from the off-gas.

It is to be understood that additional separating means can be employed to separate components from off-gas discharged from reactor 16. For example, a suitable cyclone separator, not shown, and a suitable spray drier, also not shown, can be disposed between heat exchanger 64 and scrubber 82.

Liquid composition 92 is formed by scrubbing of the off-gas with scrubber fluid 88. Liquid composition 92 is directed from scrubber 82 to reactor 12. In one embodiment, liquid composition 92 is pumped through piping 94 by pump 96 to the feed inlet tube 35. Examples of suitable pumps include a centrifugal pump, a positive displacement pump, etc. Liquid composition 92 is thereby combined with the feed for introduction into molten metal bath 44 through tuyere 28. In another embodiment, liquid composition 92 is directed through piping 97 by pump 99 to conduit 51. Liquid composition 92 is thereby combined with the feed stream for introduction into reactor 12 and onto molten metal bath 44.

At least a portion of the off-gas components are thereby returned in liquid composition 92 from the off-gas to molten metal bath 44. A substantial portion of the discharged feed components are then chemically reformed to shorter-chain unsaturated hydrocarbons, such as ethylene. Chemical reaction of the feed components in system 10 is thereby controlled.

The invention will now be further and specifically described by the following examples. All parts of percentages are by weight unless otherwise stated.

EXAMPLE 1

A 20 lb. hot metal-capacity unit was used for the experimental trials, with a susceptor/crucible arrangement used for containment and heating. The off-gas was sealed to a gas-handling train for analysis. In order to minimize the complexity associated with solids handling, isomeric surrogates of polyethylene were used. The injection was achieved by bubbling inert gas through the liquid hexane to yield an inlet concentration given by the vapor pressure of hexane. The gas mixture was subsequently bubbled into the molten metal bath, with steady state being achieved after 15 minutes.

The results of these scoping experiments are summarized in Tables 1 and 2 below.

TABLE 1

| Metal Substrate | Temperature ° C. | Feed | Concentration (%) | Ethylene Selectivity (%) |
|---|---|---|---|---|
| Brass | 1050 | n-hexane | 18 | 2 |
| Brass | 900 | n-hexane | 18 | 35 |
| Brass | 900 | n-hexane | 31 | 30 |

TABLE 2

| Metal Substrate | Temperature ° C. | Feed | Concentration (%) | Ethylene Selectivity (%) |
|---|---|---|---|---|
| Aluminum | 900 | n-hexane | 6 | <0.5 |
| Aluminum | 900 | n-hexane | 13 | 22 |
| Aluminum | 900 | 2-methyl-pentane | 18 | 19 |

EXAMPLE 2

A 20 lb. hot metal-capacity unit was used for the experimental trials, with a susceptor/crucible arrangement used for containment and heating. Various organic liquids were fed and the production of unsaturated organics was monitored. Feed addition was achieved by vaporizing the organic and sweeping it with an inert gas to achieve the desired inlet concentration. The gas mixture was subsequently added into the molten metal bath with steady state being achieved after 15 minutes. The results are summarized below.

TABLE 3

| Metal Substrate | Temperature ° C. | Feed | Concentration (%) | Ethylene Selectivity (%) |
|---|---|---|---|---|
| Copper | 900 | n-hexane | 18 | 35 |
| Aluminum | 900 | n-hexane | 13 | 22 |
| Aluminum | 900 | 2-methyl-pentane | 18 | 19 |

Equivalents

Those skilled in the art will recognize, or be able to ascertain using no more than routine experimentation, many equivalents of the invention described specifically herein. Such equivalents are intended to be encompassed in the scope of the following claims.

What is claimed is:

1. A method for reforming hydrocarbons into shorter-chain unsaturated organic compounds, comprising the steps of:

a) providing a molten metal bath, said molten metal bath consisting essentially of an elemental metal which can cause cleavage of at least one carbon-carbon bond of a hydrocarbon component of a hydrocarbon-containing feed;

b) directing said feed into the molten metal bath at a rate which causes the concentration of carbon in the molten metal bath to be lower than the saturation limit for carbon of said bath at the operating conditions of said molten metal bath, whereby the hydrocarbon component of the feed can exhibit cleavage of at least one carbon-carbon bond of the hydrocarbon component of said feed; and c) establishing and maintaining conditions in said molten metal bath to cause cleavage of at least one carbon-carbon bond of the hydrocarbon component to produce unsaturated organic compounds, as products of said cleavage.

2. A method of claim 1 wherein the molten metal bath includes a transition metal component.

3. A method of claim 1 wherein the molten metal bath provided has a melting point of greater than about 500° C.

4. A method of claim 1 wherein the molten metal bath provided has a metal equilibrium carbon solubility of greater than about 0.01% by weight.

5. A method of claim 1 wherein the hydrocarbon-containing feed is directed into the molten metal bath at a rate which causes the residence time of a carbon component of the feed to be greater than that required to cause the molten metal bath to dissolve said carbon under the operating conditions established and maintained in the molten metal bath.

6. A method of claim 5 wherein the hydrocarbon component of said feed includes an alkyl compound.

7. A method of claim 6 wherein the organic hydrocarbon component includes an alkane.

8. A method of claim 5 wherein the hydrocarbon component includes an aryl compound.

9. A method of claim 5 wherein the operating conditions of the molten metal bath include establishing and maintaining a temperature in a range of less than about 2,000° C.

10. A method of claim 9 wherein the hydrocarbon-containing feed is directed into the molten metal bath as a component of a fluid stream that includes an inert gas component.

11. A method of claim 9 wherein the concentration of the hydrocarbon-containing feed in the fluid stream is in the range of between about five and forty percent, by volume.

12. A method of claim 11 wherein the hydrocarbon is a component of oil.

13. A method of claim 11 wherein the hydrocarbon component of the feed includes polyethylene.

14. A method of claim 5 wherein a bath of molten brass is provided.

15. A method of claim 5 wherein a bath of molten aluminum is provided.

16. A method of claim 1 where the hydrocarbon-containing feed contains heteroatoms.

17. A method of claim 16 where the heteroatoms include sulfur, nitrogen, oxygen, and chlorine.

*18. An apparatus suitable for closed and sealed molten metal-based reactions comprising:*

(*a*) *an upper portion, wherein the upper portion is characterized by an off-gas outlet;*

(*b*) *a lower portion wherein the lower portion is characterized by one or more inlets having one or more lances disposed therein operably connected to an inert gas source;*

(*c*) *one or more feed inlets for the introduction of feed streams;*

(*d*) *an induction coil disposed within the lower portion;*

(*e*) *a means for controlling* (*1*) *the rate of introduction of each feed stream,* (*2*) *the rate of removal of the off gas,* (*3*) *the relative amounts of reaction components,* (*4*) *the temperature of the molten metal; and/or* (*5*) *the carbon saturation levels of the molten metal bath within residence times of between 0.1 and 5 seconds.*

*19. The apparatus of claim 18 comprising one or more feed inlets adapted for the introduction of a carbon-containing material.*

* * * * *

UNITED STATES PATENT AND TRADEMARK OFFICE

CERTIFICATE OF CORRECTION

PATENT NO. : RE42,832 E
APPLICATION NO. : 10/616797
DATED : October 11, 2011
INVENTOR(S) : Nagel et al.

It is certified that error appears in the above-identified patent and that said Letters Patent is hereby corrected as shown below:

On the Title Page:

Item [64], Replace sub-heading, PCT Filed: with sub-heading, Filed.

Signed and Sealed this
First Day of November, 2011

David J. Kappos

David J. Kappos
*Director of the United States Patent and Trademark Office*